United States Patent [19]

Shen

[11] Patent Number: 5,552,152
[45] Date of Patent: Sep. 3, 1996

US005552152A

[54] TASTE MASKING OF IBUPROFEN BY FLUID BED COATING

[75] Inventor: Robert W. Shen, Kalamazoo, Mich.

[73] Assignee: The Upjohn Company, Kalamazoo, Mich.

[21] Appl. No.: 469,715

[22] Filed: Jun. 6, 1995

Related U.S. Application Data

[63] Continuation of Ser. No. 958,070, Oct. 7, 1992, which is a continuation of PCT/US91/01089, Feb. 26, 1991, which is a continuation of Ser. No. 508,193, Apr. 11, 1990, abandoned.

[51] Int. Cl.$^6$ ............................. A61K 9/22; A61K 9/32; A61K 9/58
[52] U.S. Cl. ..................... 424/441; 424/468; 424/482; 424/497; 424/464
[58] Field of Search .................................. 424/482, 497, 424/441, 468, 464

[56] References Cited

U.S. PATENT DOCUMENTS

| | | | |
|---|---|---|---|
| 3,228,831 | 1/1966 | Nicholson | 514/568 |
| 3,385,886 | 5/1968 | Nicholson | 562/492 |
| 4,476,248 | 10/1984 | Gordon | 562/494 |
| 4,609,675 | 9/1986 | Franz | 514/568 |
| 4,800,087 | 1/1989 | Mehta | 424/497 |
| 5,084,278 | 1/1992 | Mehta | 424/441 |

OTHER PUBLICATIONS

Bakan, J. A. Microencapsulation, 1986, pp. 413–429, Part Three of "The Theory and Practice of Industrial Pharmacy".

*Primary Examiner*—James M. Spear
*Attorney, Agent, or Firm*—Thomas A. Wootton; Sidney B. Williams

[57] ABSTRACT

A chewable taste-masked ibuprofen tablet having controlled release characteristics.

6 Claims, No Drawings

TASTE MASKING OF IBUPROFEN BY FLUID BED COATING

CROSS REFERENCE TO RELATED APPLICATIONS

This application is a continuation application of U.S. patent application Ser. No. 07/958,070, filed Oct. 7, 1992, still pending, which is a continuation (national phase) of International Application No. PCT/US91/01089, filed Feb. 26, 1991, which is a continuation of U.S. application Ser. No. 07/508,193, filed Apr. 11, 1990, now abandoned.

BACKGROUND OF THE INVENTION

Ibuprofen is a well-known therapeutic agent. Its therapeutic activities include analgesia and anti-pyretic attack. As with most medicines, one of the difficulties with ibuprofen is in making it palatable to children. This difficulty has been overcome with most medicines by preparing formulations such as syrups and drops. The present invention relates to chewable tablets that are palatable to children and a process for making the tablets.

From a manufacturing cost standpoint, it is desirable to have chewable, taste-masked microcapsules that are large (0.25–1 mm in diameter), because larger microcapsules are easier to manufacture and package, and are less expensive to produce than are small microcapsules. However, an increase in size makes fracture during chewing and the release of drug from the microcapsule more likely to occur especially when there is an inadequate amount of plasticizer or other component included to provide elasticity. A larger sized microcapsule requires greater elasticity to minimize the likelihood that a fracture will occur and active agent will be released. There is therefore a need in the art of pharmaceutical formulation to provide encapsulating coatings capable of being formulated into chewable microcapsules as large as about 1.5 mm. that will not release drugs during chewing.

INFORMATION DISCLOSURE

Ibuprofen and its use for treatment of analgesia is disclosed in U.S. Pat. No. 3,385,886. Compositions containing ibuprofen and methods for using them are described in U.S. Pat. No. 3,228,831. New crystalline and high dose formulations of ibuprofen are disclosed in U.S. Pat. Nos. 4,476,248 and 4,609,675 respectively.

Microencapsulation is described by J. A. Bakan, Part Three of "The Theory and Practice of Industrial Pharmacy", 1986. pp. 413–429.

EUDRAGIT L30D is a known polymer useful for coating orally administered pharmaceutical dosage forms, particularly tablets, capsules and pills, with coatings which are resistant to gastric juices but solvent in intestinal juices.

Chewable taste-masked pharmaceutical compositions, including some containing ibuprofen, are described in U.S. Pat. No. 4,800,087. However, the compositions described therein require a coating consisting of a mixture of polymers. The use of fluidized bed for coating pharmaceutical products is described in U.S. Pat. 4,800,087.

SUMMARY OF THE INVENTION

This invention involves:

A chewable taste-masked tablet having controlled release characteristics comprising a microcapsule of about 100 microns to about 0.8 mm in diameter having (a) a pharmaceutical core including crystalline ibuprofen and (b) a methacrylic acid copolymer coating having sufficient elasticity to withstand chewing.

While chewable taste masked formulations of ibuprofen are referred to in the prior art, among the advantages of the compositions of this invention over the closest prior art compositions is that the coating used consists of a single copolymer rather than a mixture of copolymers.

DETAILED DESCRIPTION OF THE INVENTION

The present invention comprises formulations of taste-masked microcapsules which further comprise (a) a pharmaceutical core of crystalline ibuprofen and (b) a methacrylic acid copolymer coating that may provide chewable taste-masked characteristics. Both the polymeric coating and the pharmaceutical core may further comprise diluents, fillers and other pharmaceutical additives which may effect the rate of release of active ibuprofen from the microcapsule.

The methacrylic acid copolymer is preferably dispersable in water so as to take advantage of aqueous formulation techniques and has a rapid rate of dissolution at a pH of about 5.5. Aqueous-based coating systems are safe and make regulatory compliance (EPA) relatively easy compared to non-aqueous based coating systems. An elastic microcapsule which will not release ibuprofen in the mouth when chewed is contemplated by the present invention.

A preferred coating composition is a high temperature film forming polymer or "hard" polymer. A hard polymer is defined as a polymer that will form a film on a pharmaceutical core at a temperature of at least about 30° C. Examples of high temperature film forming polymers useful in this invention include hydroxypropylmethyl cellulose, for example, Pharmacoat' 606 brand from Shinetro Corp., Tokyo, Japan, hydroxypropyl cellulose, for example, Klucel' brand from Hercules Corp., Wilmington, Del., methylcellulose for example Methocel A', from Dow Chemical, Midland, Mich., ethylcellulose, for example, Ethocel' brand from Dow Chemical Corp., and other aqueous polymeric dispersions such as Aquacost' Brand from FMC, Philadelphia, Pa., and Surelease' brand from Colorcon, West Point, Pa., polyvinyl alcohol, polyvinyl acetate, cellulose acetate butyrate, styrene acylate copolymers, for example Janocryl 138 (61° C. film forming copolymer from S. C. Johnson, Racine, Wis.) and copolymers of acrylic acid esters, for example, the EUDRAGIT Copolymers (Rohm Pharma GmbH Westerstadt, W. Germany): Eudragit' L30D, Eudragit' L100-55, Eudragit' RS(30D and 100).

Eudragit' copolymers that are preferred in embodiments of this invention include L30D, an anionic copolymer based of polymethacrylic and acrylic acid esters (Methacrylic Acid Copolymer, Type C in USP XXIdNF XVI) with a mean molecular weight of 250,000.

The polymeric coating should provide for immediate release characteristics, i.e., rapid release of the active agents in the duodenum within a period of about one hour. When the microcapsules are formulated into chewable, taste-masked oral tablets or capsules, the formulations provide for immediate, rapid release in the stomach.

The chewable polymeric coating providing immediate release upon reaching the duodenum i.e., within one hour after ingestion may be comprised of a pharmaceutically compatible high temperature film forming polymer that is water insoluble or not swellable within the pH range (about 5.5–6.5) and/or the liquid content of the mouth and will not release the active agent in the mouth, but will dissolve or change in physical character in the duodenum, for example, swell or become more porous, thus releasing drug.

The most preferred film forming acrylic resin polymer that releases active agent rapidly in duodenum is EUDRAGIT L30D. EUDRAGIT L30D is a copolymer anionic in character, based on polymethacrylic acid and acrylic acid esters. Although EUDRAGIT L30D is soluble at pH's in the mouth and insoluble at pH's of the stomach, it has found usefulness in chewable, taste-masked immediate release formulations of the present invention. This usefulness may stem from the lack of liquid in the mouth, or may be the result of elastic qualifies that EUDRAGIT L30D acquires when formulated in combination with a plasticizer, or preferably, with EUDRAGIT E30D.

Any of the above described high-temperature film-forming polymers may be used for microencapsulation. However, to make capsules of the required elasticity using the above described high temperature film forming polymers, plasticizers may he incorporated into the coatings. Plasticizers useful to provide the requisite elasticity include propylene glycol and polyalkylene glycols, for example, polyethylene glycol, triacetin, (glyceryl triacetate from Eastman Kodak, Rochester, NY vinyl pyrrolidone, diethyl phthallate, dibutylsebacate, and esters of citric acid among others. Generally, the plasticizers comprise between about 2% and about 50% by weight of polymer and plasticizer combined, preferably between about 5% and 15% by weight and most preferably about 10% by weight of the polymer and plasticizer combined.

The chewable tablets of this invention are prepared by spraying a solution of the methacrylic acid copolymer on to a fluidized bed of crystalline ibuprofen.

Crystalline ibuprofen can be prepared by the process described in U.S. Pat. No. 4,476,248. The particle size of the ibuprofen should be about 80 to 500 microns and it it may contain excipients such as starch, lactose, hydroxypropyl methylcellulose, microcrystalline cellulose PVP, sucrose and fructose.

The residence time should be such that the ratio of copolymer to ibuprofen of each chewable tablet is about eight percent by weight.

The temperature of the inlet and outlet air should be maintained between 40° and 60° C. 20° and 40° C. respectively. The preferred inlet and outlet air temperatures are between 45° and 55° and 33° and 27° C. respectively.

The temperature of the fluidized bed should be maintained between 60 and $20_p$ respectively. The preferred temperature of the bed is about 35° C.

The amount of ENDRAGIT L30D in the encapsulation formulation should be between about 10% to 60% by weight of ibuprofen, preferably about 14%.

EMBODIMENT OF THE INVENTION

Example 1 Preparation of chewable ibuprofen tablet (#13, p 23)

| A. Encapsulated Ibuprofen | |
| --- | --- |
| Ibuprofen | 4 Kg |
| Eudragit L30D | 2.33 Kg (coating polymer) |
| Propylene Glycol | 140 gm (plasticizer) |
| Talc | 200 gm |
| Purified Water | 200 gm |

Ibuprofen crystals (particle size #40–105) are air suspended in a closed chamber (Glatt GPCG5). An aqueous dispersion of Eudragit L 30D and talc is sprayed onto the fluidized bed of ibuprofen at a rate of 60 gm/min. The inlet and outlet air temperature are maintained at 50° C. and 20°–22° C. respectively. The air rate is adjusted so as to maintain the particles in a suspended state and to maintain the fluidized bed at a temperature of 35° C.

Air Atomizing Pressure 3.5 bar

| B. Preparation of Chewable Tablets | Per Tab | Per 1000 Tab |
| --- | --- | --- |
| Mannitol | 5–44 mg | 544 Gm |
| Malic Acid | 4 mg | 4 Gm |
| Aspartame | 12 mg | 12 Gm |
| Spray Dried Orange Flavor | 18 mg | 18 Gm |
| Encapsulated Ibuprofen | 127 mg | 127 Gm |
| Ac-Di-Sol | 24 mg | 24 Gm |
| Avicel pH102 | 60 mg | 60 Gm |
| F.D.C. Yellow 6 Lake | 0.2 mg | 0.2 Gm |
| Citric Acid | 4 mg | 4 Gm |
| Talc | 20 mg | 20 Gm |

The compression mix of above was tabletted on a Manesty beta press with ½" flat face tooling. Tablet weight: 813 mg. Hardness: 9–13 Strong Cobert (SC). Disintegration Time in water: 2 minutes.

Table 1 shows a comparison of dissolution data between MOTRIN IB Tablet in PH 7.2 and the MOTRIN Chewable Tablets of this invention.

Table 2 shows a comparison of dissolution data between MOTRIN IB Tablets in PH 5.8 and the MOTRIN Chewable Tablets of this invention.

TABLE I

Comparison of Dissolution Data between Motrin IB and Motrin Chewable Tablets

| Buffer 7.2 PH Motrin IB Flask 1 | | #12 Flask 2 | | #13 Flask 3 | | Recrystallized Ibuprofen Raw Material Flask 4 | |
| --- | --- | --- | --- | --- | --- | --- | --- |
| Time | % Released | Time | % Released | Time | % Released | Time | % Released |
| 0.10 | −0.02 | 0.20 | 0.00 | 0.30 | 0.04 | 0.40 | −0.02 |
| 2.10 | 1.21 | 2.20 | 10.50 | 2.30 | 9.40 | 2.40 | 0.48 |
| 4.10 | 38.77 | 4.20 | 63.24 | 4.30 | 53.61 | 4.40 | 18.34 |
| 6.10 | 71.49 | 6.20 | 89.31 | 6.30 | 84.02 | 6.40 | 40.63 |
| 8.10 | 84.88 | 8.20 | 97.65 | 8.30 | 89.89 | 8.40 | 54.00 |
| 10.10 | 90.60 | 10.20 | 95.85 | 10.30 | 90.91 | 10.40 | 63.24 |
| 12.10 | 92.79 | 12.20 | 93.61 | 12.30 | 91.45 | 12.40 | 71.12 |

TABLE I-continued

Comparison of Dissolution Data between Motrin IB and Motrin Chewable Tablets

| Buffer 7.2 PH Motrin IB Flask 1 | | #12 Flask 2 | | #13 Flask 3 | | Recrystallized Ibuprofen Raw Material Flask 4 | |
|---|---|---|---|---|---|---|---|
| Time | % Released | Time | % Released | Time | % Released | Time | % Released |
| 14.10 | 93.80 | 14.20 | 91.77 | 14.30 | 91.45 | 14.40 | 78.23 |
| 16.10 | 94.36 | 16.20 | 91.38 | 16.30 | 91.62 | 16.40 | 85.25 |
| 18.10 | 94.58 | 18.20 | 91.64 | 18.30 | 91.66 | 18.40 | 87.75 |
| 20.10 | 94.67 | 20.20 | 91.86 | 20.30 | 91.68 | 20.40 | 94.43 |
| 22.10 | 94.75 | 22.20 | 91.88 | 22.30 | 91.77 | 22.40 | 96.05 |
| 24.10 | 94.77 | 24.20 | 92.01 | 24.30 | 91.79 | 24.40 | 99.24 |
| 26.10 | 94.82 | 26.20 | 92.16 | 26.30 | 91.77 | 26.40 | 100.63 |
| 28.10 | 94.88 | 28.20 | 92.40 | 28.30 | 91.79 | 28.40 | 101.32 |
| 30.10 | 94.92 | 30.20 | 92.57 | 30.30 | 91.81 | 30.40 | 101.58 |
| 32.10 | 94.95 | 32.20 | 92.79 | 32.30 | 91.88 | 32.40 | 101.71 |
| 34.10 | 95.01 | 34.20 | 92.83 | 34.30 | 91.90 | 34.40 | 102.14 |
| 36.10 | 94.99 | 36.20 | 92.92 | 36.30 | 91.86 | 36.40 | 102.20 |
| 38.10 | 95.03 | 38.20 | 92.96 | 38.30 | 91.86 | 38.40 | 102.35 |
| 40.10 | 94.99 | 40.20 | 93.00 | 40.30 | 91.84 | 40.40 | 102.46 |
| 42.10 | 95.05 | 42.20 | 93.09 | 42.30 | 91.90 | 42.40 | 102.61 |
| 44.10 | 95.10 | 44.20 | 93.15 | 44.30 | 91.92 | 44.40 | 102.66 |
| 46.10 | 95.08 | 46.20 | 93.20 | 46.30 | 91.97 | 46.40 | 102.72 |
| 48.10 | 95.10 | 48.20 | 93.24 | 48.30 | 91.97 | 48.40 | 102.74 |
| 50.10 | 95.08 | 50.20 | 93.26 | 50.30 | 91.94 | 50.40 | 102.76 |
| 52.10 | 95.14 | 52.20 | 93.26 | 52.30 | 91.94 | 52.40 | 102.79 |
| 54.10 | 95.12 | 54.20 | 93.33 | 54.30 | 92.01 | 54.40 | 102.79 |
| 56.10 | 95.14 | 56.20 | 93.35 | 56.30 | 92.03 | 56.40 | 102.89 |
| 58.10 | 95.18 | 58.20 | 93.37 | 58.30 | 92.05 | 58.40 | 102.85 |
| 60.10 | 95.18 | 60.20 | 93.41 | 60.30 | 92.05 | 60.40 | 102.92 |

In PH7.2 buffer: Formula #12 shows faster release than Motrin IB.
Formula #12, #13 and Motrin IB shows the same release rate after 10 minutes.
Formula #12, #13 all pass U.S.P. Tablets specification 20 minutes 785%.
Flask 1: Motrin IB.
Flask 2: Motrin chewable experiment Lot 12.
Flask 3: Motrin chewable experiment Lot 13.
Flask 4: Recrystallized Ibuprofen.

TABLE II

| Buffer: 5–8 PH Motrin IB Flask 1 | | #12 Flask 2 | | #13 Flask 3 | | Recrystallized Ibuprofen Raw Material Flask 4 | |
|---|---|---|---|---|---|---|---|
| Time | % Released | Time | % Released | Time | % Released | Time | % Released |
| 0.10 | 0.04 | 0.20 | 0.02 | 0.30 | 0.00 | 0.40 | 0.04 |
| 2.10 | 0.13 | 2.20 | 2.76 | 2.30 | 2.20 | 2.40 | 0.78 |
| 4.10 | 2.25 | 4.20 | 9.78 | 4.30 | 7.90 | 4.40 | 9.18 |
| 6.10 | 19.40 | 6.20 | 18.68 | 6.30 | 15.72 | 6.40 | 36.26 |
| 8.10 | 36.48 | 8.20 | 28.10 | 8.30 | 25.33 | 8.40 | 53.71 |
| 10.10 | 48.08 | 10.20 | 36.05 | 10.30 | 34.69 | 10.40 | 65.90 |
| 12.10 | 57.28 | 12.20 | 43.30 | 12.30 | 47.11 | 12.40 | 75.08 |
| 14.10 | 64.34 | 14.20 | 51.49 | 14.30 | 56.54 | 14.40 | 82.38 |
| 16.10 | 70.09 | 16.20 | 58.83 | 16.30 | 64.02 | 16.40 | 87.39 |
| 18.10 | 74.82 | 18.20 | 65.33 | 18.30 | 69.91 | 18.40 | 91.40 |
| 20.10 | 78.57 | 20.20 | 71.02 | 20.30 | 74.86 | 20.40 | 94.41 |
| 22.10 | 81.73 | 22.20 | 76.16 | 22.30 | 78.53 | 22.40 | 96.78 |
| 24.10 | 84.47 | 24.20 | 80.43 | 24.30 | 81.51 | 24.40 | 98.47 |
| 26.10 | 86.74 | 26.20 | 84.02 | 26.30 | 83.89 | 26.40 | 99.72 |
| 28.10 | 88.68 | 28.20 | 86.80 | 28.30 | 86.11 | 28.40 | 100.65 |
| 30.10 | 90.24 | 30.20 | 89.05 | 30.30 | 87.78 | 30.40 | 101.51 |
| 32.10 | 91.56 | 32.20 | 90.99 | 32.30 | 89.09 | 32.40 | 102.03 |
| 34.10 | 92.70 | 34.20 | 92.53 | 34.30 | 90.06 | 34.40 | 102.53 |
| 36.10 | 93.59 | 36.20 | 93.78 | 36.30 | 90.95 | 36.40 | 103.09 |
| 38.10 | 94.43 | 38.20 | 94.79 | 38.30 | 91.73 | 38.40 | 103.52 |
| 40.10 | 95.21 | 40.20 | 95.62 | 40.30 | 92.46 | 40.40 | 103.91 |
| 42.10 | 95.75 | 42.20 | 96.26 | 42.30 | 93.00 | 42.40 | 104.34 |
| 44.10 | 96.29 | 44.20 | 96.76 | 44.30 | 93.50 | 44.40 | 104.67 |
| 46.10 | 96.67 | 46.20 | 97.17 | 46.30 | 93.84 | 46.40 | 105.08 |
| 48.10 | 96.95 | 48.20 | 97.45 | 48.30 | 94.15 | 48.40 | 105.25 |
| 50.10 | 97.21 | 50.20 | 97.65 | 50.30 | 94.36 | 50.40 | 105.46 |

TABLE II-continued

| Buffer: 5–8 PH Motrin IB Flask 1 | | #12 Flask 2 | | #13 Flask 3 | | Recrystallized Ibuprofen Raw Material Flask 4 | |
|---|---|---|---|---|---|---|---|
| Time | % Released | Time | % Released | Time | % Released | Time | % Released |
| 52.10 | 97.54 | 52.20 | 97.88 | 52.30 | 94.60 | 52.40 | 105.72 |
| 54.10 | 97.75 | 54.20 | 98.12 | 54.30 | 94.77 | 54.40 | 105.94 |
| 56.10 | 97.97 | 56.20 | 98.25 | 56.30 | 94.97 | 56.40 | 106.11 |
| 58.10 | 98.12 | 58.20 | 98.38 | 58.30 | 95.08 | 58.40 | 106.29 |
| 60.10 | 98.27 | 60.20 | 98.47 | 60.30 | 95.18 | 60.40 | 106.37 |

PH 5–8: After 10 minutes 10–12% difference action compare #12, #13 with Motrin IB.
After 20 minutes about 7–8% difference when compared #12, and #13 with Motrin IB.
After 30 minutes shows no significant difference among them.
Flask 1: Motrin IB.
Flask 2: Motrin chewable experiment Lot 12.
Flask 3: Motrin chewable experiment Lot 13.
Flask 4: Recrystallized Ibuprofen.

I claim:

1. A chewable taste-masked tablet having controlled release characteristics consisting essentially of a microcapsule of about 100 microns to about 0.8 mm in diameter having (a) a pharmaceutical core including crystalline ibuprofen and (b) a methacrylic acid copolymer coating having sufficient elasticity to withstand chewing.

2. A chewable taste-masked pharmaceutical composition according to claim 1 wherein the copolymer is a copolymer of polymethacrylic acid and acrylic acid esters said coating being adapted to release said ibuprofen in the duodenum.

3. The composition according to claim 1, wherein said copolymer coating further comprises a plasticizer.

4. The composition according to claim 2, wherein said copolymer coating further comprises a plasticizer.

5. The composition according to claim 4, wherein said plasticizer is selected from the group consisting of glyceryl triacetate, triethyl citrate, acetyl triethyl citrate, dibutyl sebacate, acetyl tributyl citrate, diethyl phthlate, dibutyl phthlate, glycerine, propylene glycol and polyethylene glycol.

6. The composition according to claim 5 wherein said plasticizer is propylene glycol.

* * * * *